United States Patent
Buch-Rasmussen et al.

(10) Patent No.: US 6,461,334 B1
(45) Date of Patent: Oct. 8, 2002

(54) MEDICAL ARTICLE WITH COATED SURFACES EXHIBITING LOW FRICTION AND PROTEIN ADSORPTION

(75) Inventors: Thomas Buch-Rasmussen, Gentofte (DK); Patric Jannasch, Roskilde (DK); Erling Bonne Jørgensen, Veskø (DK); Ib Johannesen, Værløse (DK); Sokol Ndoni, Copenhagen S (DK)

(73) Assignee: Novo Nordisk A/S, Bagsvaerd (DK)

( * ) Notice: Subject to any disclaimer, the term of this patent is extended or adjusted under 35 U.S.C. 154(b) by 0 days.

(21) Appl. No.: 09/260,758

(22) Filed: Mar. 2, 1999

Related U.S. Application Data
(60) Provisional application No. 60/087,573, filed on Jun. 1, 1998.

(30) Foreign Application Priority Data

Mar. 6, 1998 (DK) .................................... PA1998 0307
May 28, 1998 (DK) .................................... PA1998 00731

(51) Int. Cl.[7] ............................................. A61M 5/315
(52) U.S. Cl. .................................... 604/230; 427/2.1
(58) Field of Search .................. 604/230, 403, 604/416; 361/225, 226, 230; 204/164–165, 167–169, 192.15, 192.16, 192.23; 427/2.1, 2.24–2.26, 2.28, 2.29, 2.3, 2.31

(56) References Cited

U.S. PATENT DOCUMENTS

| | | | | |
|---|---|---|---|---|
| 3,935,342 A | * | 1/1976 | Lim | 427/341 |
| 4,767,414 A | * | 8/1988 | Williams et al. | |
| 4,842,889 A | | 6/1989 | Hu et al. | |
| 4,844,986 A | | 7/1989 | Karakelle et al. | |
| 5,280,084 A | * | 1/1994 | Paul | 427/299 |
| 5,338,312 A | * | 8/1994 | Montgomery | 604/230 |
| 5,871,823 A | * | 2/1999 | Anders et al. | 427/322 |

FOREIGN PATENT DOCUMENTS

| | | |
|---|---|---|
| AU | 603862 | 8/1989 |
| EP | 0 338 418 | 10/1989 |

OTHER PUBLICATIONS

JP 9324171—Nippon Sheet Glass Co. Ltd., Dec. 16, 1997.

* cited by examiner

Primary Examiner—Brian L. Casler
Assistant Examiner—Catherine Serke
(74) Attorney, Agent, or Firm—Skadden, Arps, Slate, Meagher & Flom

(57) ABSTRACT

The present invention relates to a medical article for containing a pharmaceutical protein preparation comprising at least a first component and a second component, having at least one surface coated with a coating to reduce the friction between the two components and to reduce the protein adsorption to the coating. The coating is a hydrophilic coating whereby the hydrophilicity of the surface of the coating as measured by the water contact angle is below 90°, and the long term static friction forces between the first and the second component are below 14 N. The coatings according to the present invention are especially suited for permanently coating in ternal surfaces of containers equipped with stoppers for storage and administration of liquid protein preparations, such as insulin preparations. The coating is preferably a silicon-containing coating, such as a poly (dialkyl siloxane) oil or copolymer. The invention further relates to a process of producing a component of a medical article coated as described above, comprising adding the coating material to the component material prior to molding and subsequently molding the component from the mixture, or molding the component from the component material and subsequently applying the coating material to the at least one surface of the component, and hydrophilizing the coating material prior to the molding or after the molding. Also the invention relates to a coating as defined above for articles having at least a first component and a second component.

44 Claims, 4 Drawing Sheets

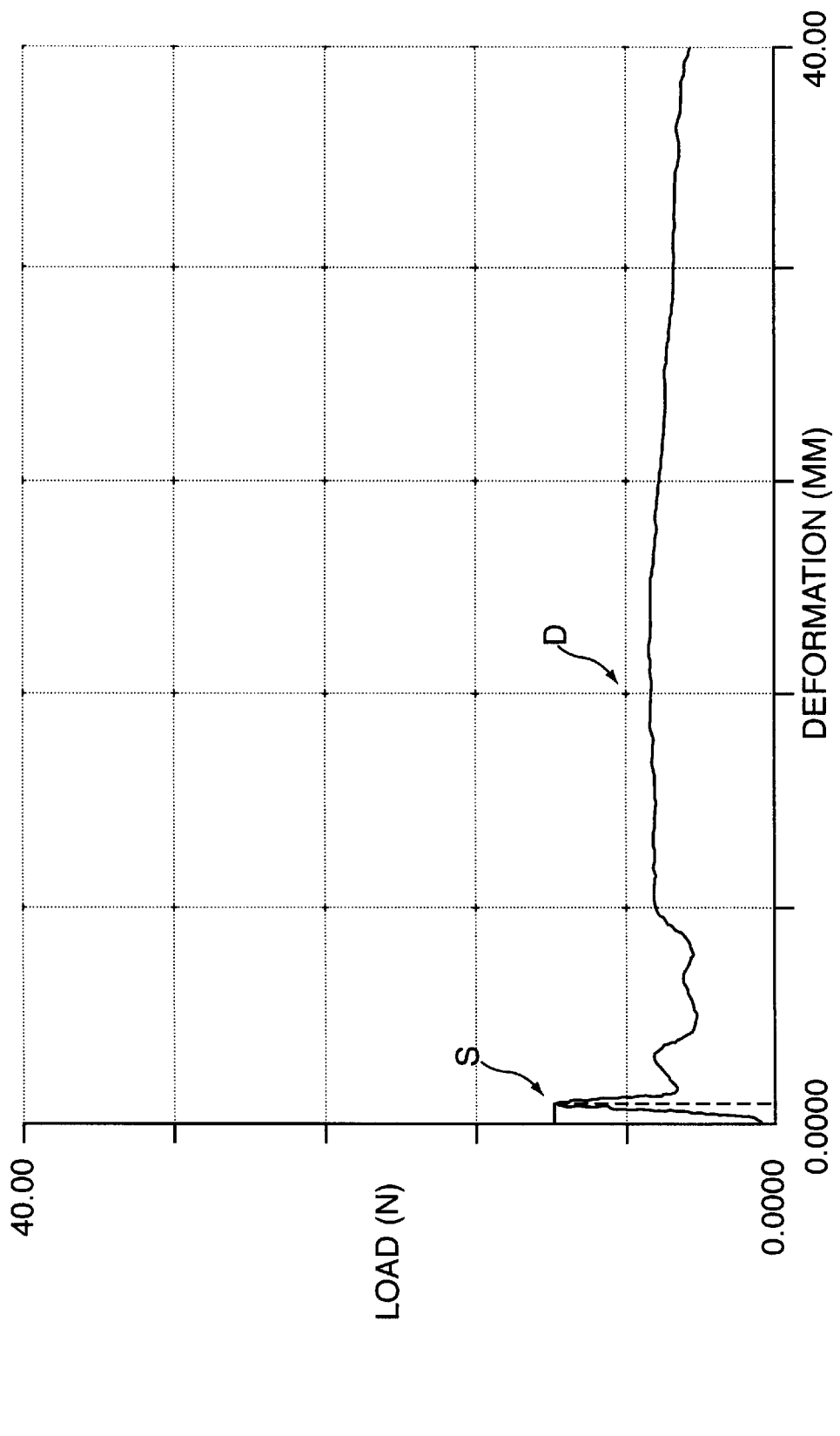

Figure 1A:
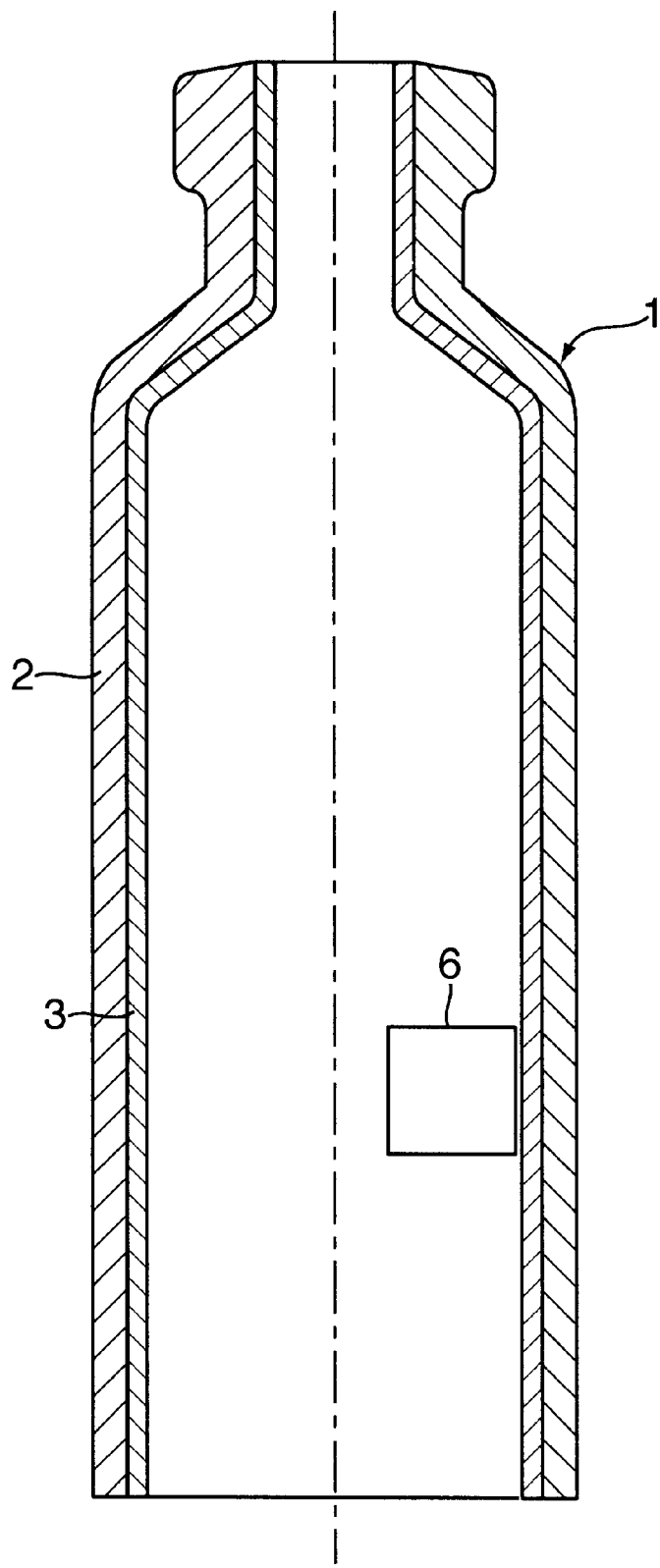

MEDICAL ARTICLE WITH COATED SURFACES EXHIBITING LOW FRICTION AND PROTEIN ADSORPTION

CROSS-REFERENCE TO RELATED APPLICATIONS

This application claims priority under 35 U.S.C. 119 of Danish applications PA 1998 0307 and PA 1998 00731 filed Mar. 6, 1998 and May 28, 1998, and U.S. Provisional application No. 60/087,573 filed Jun. 1, 1998, the contents of which are fully incorporated herein by reference.

The present invention relates to a medical article for containing a pharmaceutical protein preparation comprising at least a first component and a second component, having at least one surface coated with a coating to reduce the friction between the two components and to reduce the protein adsorption to the coating.

The described coatings are particularly useful for coating containers for storage and administration of liquid protein solutions, such as insulin formulations.

BACKGROUND

Protein formulations are mostly dosed from relatively small containers, i.e. up to 5 ml, and many of the containers are designed for multiple dosages, each dosage often being in the range of 0.1 ml or even less.

Such containers equipped with stoppers require a smooth sliding movement of one component, e.g. a stopper, in contact with another component, e.g. a container wall, to provide reliable dosages with high precision. Often, surfaces of the components have been shown to develop an initial resistance to movement after being in contact for some time, and movement does not start until a certain applied force, hereafter called a static friction force, has been applied. The phenomenon causes a sudden, rapid relative movement of the two surfaces. Frequently, the movement stops and another resistance is built up. This kind of movement is generally known as the 'slip-stick' phenomenon and is caused by a degree of adhesion between the components. When the "slip-stick" phenomena occurs with coated components, most often it is due to migration of the coating, leaving two components in contact with each other. The "slip-stick" causes a problem in that it leads to irregular and imprecise dosages. The phenomenon is especially troublesome in dispensing devices where very small, drop-wise dosages of protein solutions, e.g. insulin formulations, are required. If the 'slip-stick' phenomenon does not occur when the surfaces start to slide after the static friction force has been applied, the surfaces slide at a smoother rate by application of a so-called dynamic friction force.

Today large amounts of insulin are sold in dispensing devices. The insulin is filled in glass containers, which are equipped with rubber stoppers, and these containers are then loaded into dispensing devices. Usually, both the glass containers and the rubber stoppers are coated with silicon oil, poly(dimethyl siloxane) (PDMS), to reduce the friction between the container wall and the stopper. One common method to coat glass containers with silicon oil is to apply a PDMS-in-water emulsion and subsequently evaporate the water in an oven.

For example U.S. Pat. No. 4,767,414 suggests a coating of a medical container having reduced friction between the components wherein a surface is plasma-treated as well as a lubricant at one of the components is plasma-treated to inhibit migration of the lubricant into the content of the container. The lubricant is disclosed to reduce the friction between a container wall and a stopper compared to untreated containers and stoppers. The reference does not discuss adherence of proteins.

Another reference U.S. Pat. No. 5,338,312 discloses an article having a coating with two or more layers of lubricant securing a low friction force at different movement velocities, in that one layer may secure low friction at low velocities and the other(s) at other velocities. The adherence of protein molecules to the coating is not disclosed.

An aspect, which should be considered, when dispensing protein formulations is the events occurring at the surface between the protein solution and the container material that play a crucial role for the overall performance of biological material. Especially if the drug is in contact with a packaging material for a long time during storage which is often the case with protein formulations that are filled into the containers immediately after molding of the containers, the stability and life-time of the drug will be affected. The primary reason for this is that protein may be adsorbed to the surfaces of the container, where it is deactivated or denaturated. In this way, layers of deactivated and inaccessible protein are built up at the container surface. This will lead to a loss in protein activity and an enhanced risk of incorrect dosage, due to lowering of the concentration of soluble protein.

In particular in respect of insulin, adsorbed insulin may desorb and some molecules will associate with other deactivated molecules and form aggregates. Aggregates, such as fibrils or gel-like particles, form as a result of lower degree of water solubility and aggregation after denaturation. Aggregation of insulin is thought to be an auto-catalyzed process, and leads to an overall destabilization of the insulin formulation. When these aggregates become large enough, they can be seen visually. By blocking the adsorption of insulin at the container surface, the propensity of the insulin molecule to change its conformation is removed. The result is a significant improvement of the drug stability. Furthermore, the presence of protein aggregates may lead to immunological reactions in the patient, which is unacceptable.

In the prior art, solutions to the adsorption problem have been attempts to increase the stability of different insulin formulations by adding to the protein formulation a stabiliser.

Addition of glycerol and certain polysaccharides are well known methods to improve the stability. Further, addition of zinc and calcium ions significantly stabilizes the insulin by promoting the formation of more stable species, i.e., dimers and hexamers. It is also known that low concentrations of lecithins or synthetic detergents has a markedly positive effect on the stability of insulin. This effect is thought to be coupled to their ability to cover hydrophobic domains exposed by the insulin molecules. These hydrophobic domains are thought to be involved in the destabilization of insulin.

In relation to insulin, different kinds of non-ionic surfactants have been used to stabilize insulin formulation, e.g., ethoxylated fatty acids and Pluronics®. Chawla et al. (Diabetes Vol 34, May 1985, pp 420–424) was able to stabilize insulin in PS and PP containers by adding Pluronic® F68, a non-ionic surfactant containing PEO. These types of molecules are however only loosely adsorbed to the surfaces, and are probably present in the insulin solution which results in injection of the polymer when the protein formulation is injected. It is therefore unclear whether the surfactants cover the hydrophobic domains of the insulin, or the hydrophobic plastic surface. Chawla et al. also found that other types of Pluronics®, 17R8 and 25R5, did not stabilize the insulin formulations.

As previously mentioned, also U.S. Pat. No. 4,767,414 and U.S. Pat. No. 5,338,312 (vide above) are both silent with respect to adsorption of the content to the coating and do not suggest any solution to that problem.

Accordingly, it is an object of the present invention to provide a medical article being coated with a coating whereby the exposed surface of the coating is hydrophilic thereby reducing the protein adsorption, in particular insulin, and said surface also exhibits a lubricity resulting in reduced friction at surfaces being in frictional engagement with each other.

Furthermore, it is of importance that the coating of the surfaces of the article will not migrate into the content of the article.

SUMMARY OF THE INVENTION

The object of the invention is obtained by a medical article for containing a pharmaceutical protein preparation comprising at least a first component and a second component, which is in frictional engagement with said first component, wherein at least one surface on either the first or the second component or both is coated independently with a hydrophilic coating whereby the hydrophilicity of the surface of the coating as measured by the water contact angle is below 90°, and the long term static friction forces between the first and the second component are below 14 N.

The coatings according to the present invention are especially suited for permanently coating internal surfaces of containers equipped with stoppers for storage and administration of liquid protein preparations, such as insulin preparations.

The term "frictional engagement" is used with its normal meaning.

Furthermore, in the present context, by the term "long term static friction forces" is meant the friction forces necessary to move the two components relative to each other measured after a resting period of at least 14 days after the components have been brought into frictional engagement with another. Furthermore, by the present coating the "slip-stick" phenomenon is substantially eliminated.

The coating(s) provide low friction between the two components, such as a container wall and a rubber stopper, resulting in high-precision dosing. In addition, they efficiently prevent the adsorption of protein to the container surface, thereby increasing the stability and prolonging the storage time of the protein.

Another object of the invention is a process of producing a component of a medical article coated as described above, comprising adding the coating material to the component material prior to molding and subsequently molding the component from the mixture, or molding the component from the component material and subsequently applying the coating material to the at least one surface of the component, and hydrophilizing the coating material prior to the molding or after the molding.

A third object of the invention is a coating as defined above, for articles having at least a first component and a second component, said second component being in frictional engagement with said first component, wherein at least one surface or either the first or the second component or both is coated independently with a hydrophilic coating.

DRAWINGS

FIG. 1A is a longitudinal sectional view of a first component, in the form of an injection cylinder, according to the invention.

Figure 1B:
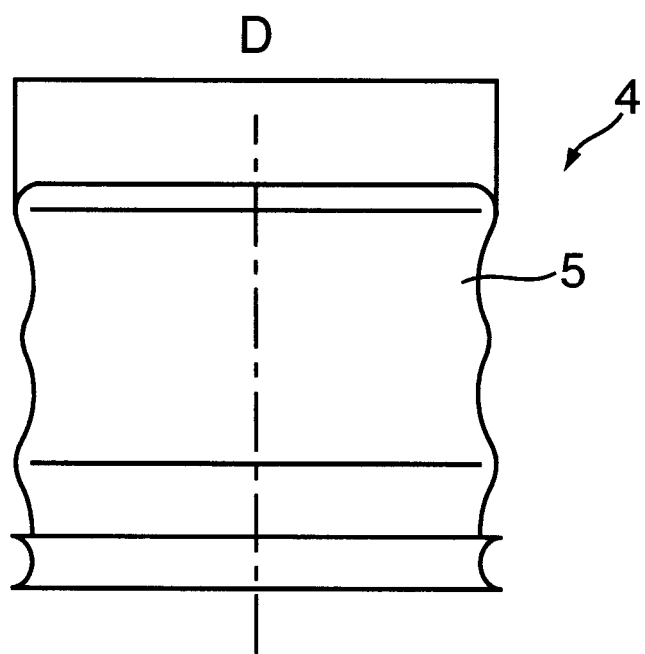

FIG. 1B is a side view of a second component, in the form of a plunger. The inner diameter of the first component is 9.23 mm and the outer diameter is 11.0 mm. The outer diameter D of the second component is 9.6 mm.

Figure 3:
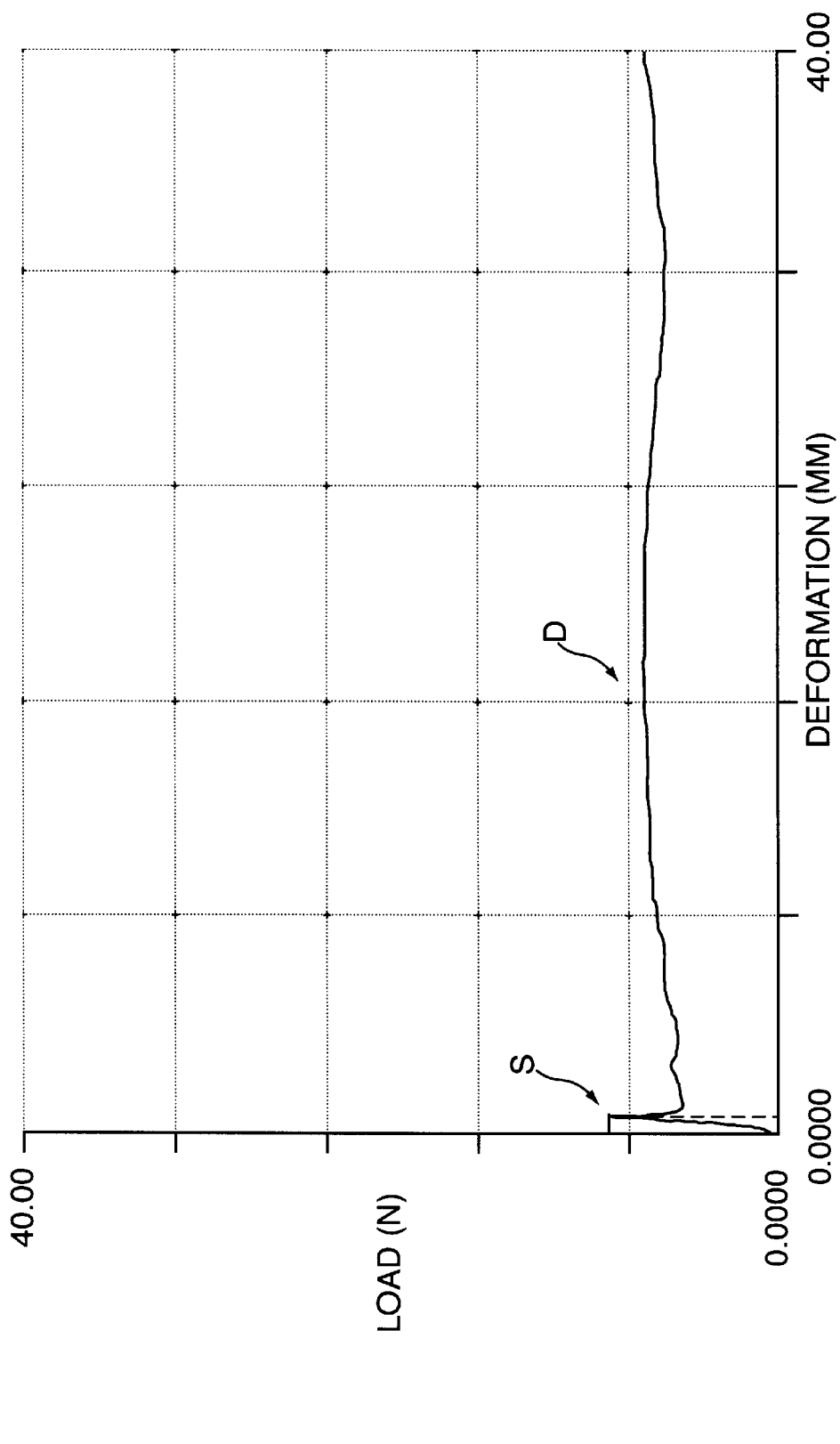

FIG. 2 and FIG. 3 show the result of recordings of friction forces where the maximum static forces are indicated with S and the maximum dynamic friction forces are indicated with D for a medical article coated with two different coatings as described in the examples.

DETAILED DESCRIPTION OF THE INVENTION

The present invention relates to a medical article for containing a pharmaceutical protein preparation comprising at least a first component and a second component, such as a container and a stopper, which is in frictional engagement with each other, wherein at least one surface on either the container or the stopper or both is coated independently with a hydrophilic coating whereby the hydrophilicity of the surface of the coating as measured by the water contact angle is below 90°, and the long term static friction forces between the first and the second component are below 14 N.

The coating according to the present invention is hydrophilic, or at least the surface part of the coating exposed to the content is hydrophilic. Without being bound by theory it is believed that hydrophobic domains on the protein molecule is responsible for the protein adsorption, and hence, that a certain hydrophilic surface of the coating reduces the adsorption tendency.

Accordingly, the present invention relates to a medical article coated with a coating which is hydrophilic to such an extent that the protein adsorption, in particular the insulin absorption is significantly reduced or substantially eliminated. For the inventive coating the hydrophilicity as measured by the water contact angle is below 90°.

The water contact angle is preferably below 60°, more preferably below 20°, most preferably below 10°, in order to secure a low protein adsorption.

The amount of protein adsorbed to the coating depends on the concentration of protein solution as well as the surface area of the coating in contact with the protein solution.

In the present context, a measure of the protein adsorption is obtained by measuring by the insulin adsorption in a container with a standard volume of 3.5 ml, and an internal surface area of 14.1 $cm^2$ by the procedure as described in example 2.

The protein adsorption measured under these conditions is preferably less than 0.5%, such as less than 0.4%, most preferably less than 0.3% of the original protein solution.

Insulin stability may be measured by assembling containers and plungers, and subsequently filling the container with Penmix 30/70®. After closing the container with a bromobutyl plate and an aluminum cap, the containers are stored at 37 degree Centigrade and rotated vertically 4 h every 24 h at 30 rotations per minute. The experiment is stopped at the specified time, and the insulin is acidified by an aqueous HCl solution. The remaining percentage of monoinsulin, as compared to the original amount, may be detected by GPC (gel permeation chromatography), and used as a parameter to describe the remaining insulin activity.

According to the invention any hydrophilic coating exhibiting the low protein adsorption, especially insulin adsorption, may be used for coating the surface of the medical article provided the long-term static friction forces between the first and the second component are below 14 N.

The coating according to the present invention has a reduced ability of migrating, because it is preferably essentially a solid material and not an oil or a liquid. Furthermore, the coating is preferably fixed to the component.

By reducing the ability of migrating the coating does not migrate from the interface between the two components during storage hence the slip-stick phenomenon is significantly reduced or eliminated whereby a high-precise dosing is possible, in particular when dosing small volumes, such as when dosing insulin.

Also, the reduced migration tendency reduces the risk of having particles of the coating solubilised or suspended in the protein formulation.

In a preferred embodiment of the invention the coating material is not not capable of forming an emulsion with the solvent of the protein formulation, such as water, and is not soluble in water.

The coating is preferably a silicon-containing coating, such as a poly(dialkyl siloxane) oil or copolymer. In a preferred embodiment the poly(dialkyl siloxane) is selected from poly(dimethyl siloxane) (PDMS), poly(dipropyl siloxane) or poly(dihexyl siloxane).

The viscosity of the oil when applied to the component is of importance, especially for the elimination of the slip-stick phenomenon. The more viscous the lesser the risk of a slip-stick phenomenon. In one embodiment of the invention the coating comprises a linear or branched hydrophilized poly(dialkyl siloxane) oil. The viscosity of the oil is preferably above 200,000 centistokes, such as above 500,000 centistokes when applied to the component.

In a preferred embodiment of the invention the coating comprises a crosslinked or gelled silicon oil, such as a hydrophilized poly(dialkyl siloxane) oil, or a mixture of a crosslinked and a non-crosslinked oil. By using a crosslinked or gelled oil the migration ability of the oil is significantly reduced and the viscosity increased towards infinitely great, i.e. the oil may broadly be looked upon as a solid material.

A cross-linked, or cured, silicon oil is typically obtained by applying a linear, or branched, silicon oil with reactive functionalities which are used to cross-link the coating in a subsequent step. There are a number of different available cross-linking methods, e.g. curing by irradiation with UV light, curing in an oven at elevated temperature, and curing in the presence of water. Preferably the cross-linkable silicon oil is of medical grade, e.g. MDX® supplied by Dow Corning (MDX4-4159 Fluid). A cross-linked silicon oil may also be obtained by first applying a silicon oil, linear or branched, and secondly irradiating the oil by a high-energy radiation source, e.g. an electron or x-ray source.

In a more preferred embodiment of the invention the coating comprises a hydrophilized poly(dialkyl siloxane) block and graft copolymer.

The copolymer may be any block and graft copolymer which comprises polymeric segments of poly(dialkyl siloxane), such as PDMS. The polymeric segments may, for example, be combined with polymeric segments of polystyrene, polyolefins, polyamides, or polyurethane to form the desired copolymer. The copolymer may be prepared by any method available, for example by sequential anionic polymerization, or different grafting procedures.

The hydrophilicity of the coating according to the invention may be obtained by any appropriate method. In a preferred embodiment of the invention the coating is subjected to an oxidative treatment, such as plasma treatment or corona treatment after having been applied to the component.

In another preferred embodiment the coating comprises a copolymer which is made hydrophilic by end-capping the copolymer with hydrophilic group or chain segments.

The hydrophilic group may, for example, be a negatively charged chemical group or phosphorylcholine (PC) groups, and the chain segment may, for example, be poly(ethylene oxide) (PEO) or poly(2-hydroxyethyl methacrylate) (pHEMA).

The plasma treated surfaces may be modified in order to further decrease the protein adsorption by coupling of hydrophilic polymer segments or functional groups. These polymer segments or functional groups may be of the same kind as those described above, and may further be coupled to the functional groups generated during the plasma treatment.

Depending on the migration ability of the coating the hydrophilic groups at the coating will tend to seek into the coating leaving the surface hydrophobic due to the hydrophobicity of the surrounding air. Accordingly, it is of great importance that the coating remains hydrophilic during storage until the medical article is filled with the protein solution. This may be secured by placing the coated article in a hydrophilic environment, such as by filling the medical article with the protein formulation shortly after the coating process.

The thickness of the coating depends on the specific coating, and is preferably from 0.005 to 10 $\mu$m, more preferably from 0.01 to 1$\mu$m. The optimal thickness depends on the dimensions and shape of the components, and it can easily be performed by one skilled in the art. If the coating is too thin the coating may be torn in use, thereby increasing the friction between the two components. When the thickness of the coating has reached a certain plateau value the friction forces are approximately constant even when the thickness is further increased. For any coating composition the coating is preferably as thin as possible to reduce the costs. The thin coating is preferably from 0.005 to 0.4 $\mu$m, such as from 0.015 to 0.25 $\mu$m, more preferably approximately 0.2 $\mu$m.

The medical article may be any article wherein two components are in frictional engagement with each other, such as a syringe and plunger, in particular a cartridge with a stopper. The particular form or shape of the components of the article is not crucial for the present inventionen, as long as they fulfill the criteria for their use, e.g. container and fluid-tight stopper in frictional engagement.

The first component is preferably a container, such as a cartridge made of a material selected from glass, ceramic, metal and preferably plastic. In case of a container made of plastic, the plastic may be filled with inorganic or organic filler. Preferably, the first component is made of plastic material which is an excellent barrier against the contents of the protein solution, e.g. water and preservatives. Several different such plastic materials are commercially available, e.g. polypropylene, cyclic polyolefins, polyester resin.

The second component is preferably a stopper at least partly made of a flexible material, such as for example a stopper made of any appropriate material with only the contacting surfaces made in a flexible material, such as rubber. An example is a stopper with an O-ring. The stopper may also be made totally of a flexible material, such as rubber. Several suitable rubber materials are available on the market, such as bromobutyl, Santoprene®, and Trefsin®.

The article may further comprise mixing means. It is preferred that the surface of the mixing means is at least partly coated with a coating as defined above. This is especially to reduce the protein adsorption to the mixing means, but it is also of importance that the friction between the mixing means and the other components is reduced.

The medical article according to the present invention is preferably a container 1 and a stopper 4 as depicted in FIG. 1A and FIG. 1B comprising the cylinder wall 2 and a coating 3 on the inner surface of the cylinder wall 2. FIG. 1A also shows schematically a mixing means 6 within the container 1.

In FIG. 1B the stopper 4 is depicted with a rubber end 5 to be inserted in the injection cylinder 1. The diameter D of the stopper is slightly greater than the inner diameter of the injection cylinder to obtain a sufficient liquid tight sliding engagement.

The medical article is preferably constructed to avoid leakage of the liquid protein formulation, in particular without leakage between the stopper and the container wall. This is a problem in particular encountered with a container for storing and administrating (injecting) the formulation because the container is filled with the formulation and stored for a longer period before use. Accordingly, the pressure of the stopper against the container wall is adjusted to withstand leakage.

The coating may be applied either on both the components, in any combination, or on only one of the mentioned surfaces. Also, a coating according to the invention may be applied on one of the surfaces, while the other surface is coated with untreated, i.e. not hydrophilized linear or branched silicon oil. Preferably, at least the component having the largest surface area in contact with the protein formulation is coated according to the invention.

Preferably, the coating is applied to substantially all the surfaces to be in contact with the protein solution, in order to reduce the risk of destabilisation of the protein solution. Furthermore, in order to maintain the low friction and reduced slip-stick phenomenon at any stage of frictional engagement between the two components the coating should be applied to the all the surfaces of at least one component to be in frictional engagement with the other component.

In a preferred embodiment the coating on the first component is different from the coating on the second component, at least at the surfaces to be in frictional engagement with each other.

The coating on the first component and the second component may comprise, for example a hydrophilized poly(dialkyl siloxane) oil and a hydrophilized cross-linked poly(dialkyl siloxane) oil, respectively, or hydrophilized block copolymer and hydrophilized poly(dialkyl siloxane) oil.

The object of the present invention is also achieved by a medical article according to the invention coated with a hydrophilic coating on one component and on the other component coated with a coating responsible or substantially responsible for the low friction forces.

The static friction force between the first component and the second component increases gradually with the storage time from the moment of frictional engagement of the two components to reach a plateau value approximately 14 days after assembling of the components. Thereafter the static friction force is approximately constant. Accordingly, the static friction force measured 14 days after assembling the two components, such as placing a stopper in a container, can be taken as a measure of the long-term static friction forces.

In a medical article according to the invention the long-term static friction forces between the first and the second component are below 10 N, preferably below 8 N, more preferably below 6 N.

Every time the movement of the two components relative to each other stops the static friction forces start to build up again, approaching the plateau value. For a medical multi-dose article for injecting a drug solution this means that after each dosing of the drug the static friction forces are build up again.

The dynamic friction force should preferably be as close to the static friction force as possible to secure an even movement of the second component relative to the first component during an injection. In a preferred embodiment the dynamic friction forces between the first and the second component are below 8 N, such as 6 N, more preferably below 4 N.

The long-term static friction forces as well as the dynamic friction forces depend on the dimensions of the two components. In the present context the long-term static friction forces are measured with a container as described in the Examples.

Another aspect of the present invention is a process of producing a component coated as described above said process comprises adding the coating material to the component material prior to molding and subsequently molding the component from the mixture, or molding the component from the component material and subsequently applying the coating material to the at least one surface of the component, and hydrophilizing the coating material prior to the molding or after the molding.

The components of the medical article may be molded by any suitable process, such as injection molding.

In one embodiment the coating is applied to the component after the molding of said component. The coating may be applied by any appropriate method, such as dip coating, spray coating or plasma polymerisation. The coating material is preferably applied as a solution and the solvent removed after application, e.g. by evaporation.

Depending on the specific type of coating a hydrophilisation step may be accomplised prior to or after molding. When the coating comprises a copolymer being hydrophilised by end-capping the hydrophilisation step is preferably carried out prior to the coating step.

In any case, the hydrophilisation may take place as described above.

In another embodiment the component material and the coating material is mixed before molding and molded as a mixture. In this case, the coating material preferably comprises a copolymer, such as a polyolefin-PDMS block copolymer end-capped with a hydrophilic segment or group. During the molding process the coating material will make for the surface of the component forming a coating fixed to the component.

The present invention is further discussed below in Examples, which are not intended in any way to limit the scope of the present invention.

EXAMPLES

Polypropylene (PP) containers, depicted in FIG. 1A, with a volume of 3.5 ml, and an internal surface area of 14.1 cm$^2$, having an inner diameter of 9.44 mm were used in the evaluation of the different coatings. The diameter D of the stopper was 9.6 mm. Polypropylene (PP) and bromobutyl rubber represents model materials for the container and stopper in the examples. The used silicone oils were Dow Corning DC360 fluid® (DC360) and Dow Corning MDX4-4159 fluid® (MDX). The molecular data of the polystyrene-polydimethylsiloxane (PSPDMS) block copolymer used are shown in Table 1 below. These types of copolymers can be prepared by well-known methods by one skilled in the arts.

TABLE 1

| Block copolymer designation | Molecular weight of the PDMS bloc (kg/mol) | Molecular weight of the PS block (kg/mol) | PDMS content of the copolymer (wt %) |
| --- | --- | --- | --- |
| BCP5 | 250 | 250 | 50 |

Coating Procedure

PP containers and rubber plungers were coated with silicone oil (MDX and DC360) by a dip coating method. The containers were dip coated in heptane solutions of the silicone oils, and the rubber plungers were dip coated in a Dow Corning OS10® fluid solution of the silicone oils. The concentrations were 1% (w/v) for DC360, and 1+1% (w/v) for the mixture of DC360 and MDX. PP containers were also dip coated in chloroform solutions (1% w/v) of the polystyrene-polydimethylsiloxane (PSPDMS) block copolymer. The dip coated samples were left to dry in air at ambient temperature.

Curing Procedure

Coatings containing MDX were cured by storing the coated containers in an oven at 40° C. for 10 days. A cup of water was placed in the oven to maintain a relative humidity above 30% during the curing.

Plasma Treatment

The plasma treatments were performed by using a laboratory set-up. The gas used in the treatment was a mixture consisting of 80% argon and 20% oxygen. The equipment was operated at 40 W, at a pressure of 0.5 bar for 1.5 min.

Example 1

Friction Measurements

Two medical articles were coated according to the invention, the coating was as specified below in Table 2 and one article coated as comparison without hydrophilisation. The friction measurements were carried out as follows: After coating, drying, and in some cases curing, the plungers and the containers were assembled. The containers were filled with a commercial liquid insulin solution (Actrapid®) from Novo Nordisk A/S, Penmix 30/70 ), sealed with aluminum caps, and stored at 37° C. After the storage period, the aluminum caps were removed and the dynamic and static friction forces between the plungers and the containers were evaluated by using a Lloyds tensile tester at a constant displacement speed of 100 mm/min. The plunger was pushed down through the container by the tensile tester, and the force to do so was recorded as a function of the displacement. The maximum static friction force was taken as the peak friction force reached shortly after the plunger begins to move, and the maximum dynamic friction force was taken as the maximum friction force reached after the maximum static friction force had been recorded. The friction forces were measured immediately after assembling, and after 14 days to evaluate the influence of storage time on the friction forces. The results are shown in FIG. 2 and FIG. 3.

Water contact angle measurements were carried out with a Leitz sessile drop contact meter at ambient temperature. A 5 microliter droplet of Milli-Q water were pumped out onto the surface be means of a microsyringe, and the advancing angles were measured. Receding contact angles were measured after the droplet had been in contact with the surface for 60 sec. At least four measurements were made on different positions on each plate.

The maximum friction forces measured after 14 days of storage as well as the water contact angle of the coating at the container are shown in table 2.

TABLE 2

| Coating on container | Coating on plunger | Measurements of maximum friction forces (N) | | Water contact angle (°) |
| --- | --- | --- | --- | --- |
| | | Static (S) | Dynamic (D) | |
| MDX and DC360 (comparison - no hydrophilisation) | DC360 | 10.0 | 8.0 | 105 |
| MDX and DC360/plasma treated | DC360 | 12.01 | 7.0 | <10 |
| MDX and DC360/plasma treated | BCP5 block copolymer | 9.2 | 7.0 | <10 |

As may be seen all the medical articles exhibit acceptable friction measurement values, but the comparison article exhibit unacceptable water contact angle value.

Example 2

Protein Adsorption

Two of the medical articles coated as specified in example 1 were used in protein adsorption studies exemplified as insulin adsorption carried out as follows: Insulin adsorption was measured by filling coated containers with $^{125}$I-labeled Novo Nordisk Penmix 30/70® insulin with a protein activity of 100 U/ml, and a radio activity of 3.9 microCi/ml. After storage for 14 days at 37° C. the γ-counts per minute (CPM) of the protein solutions in the containers were measured. The containers were subsequently emptied, and washed 5 times with Milli-Q water. The CPM of the washed containers were measured, and the insulin adsorption is reported as percentage of the original insulin solution detected on the ampoules after washing. The average value from measurements on five containers is reported for each given adsorption value. The water contact angle was measured as specified in example 1.

The results are shown below.

TABLE 3

| Coating on container | Coating on plunger | Water contact angle (°) | Protein adsorption (%) |
| --- | --- | --- | --- |
| MDX and DC360/(comparison - no hydrophilisation) | DC360 | 105 | 0.33 |
| MDX and DC360/plasma treated | DC360 | <10 | 0.23 |

As may be seen from table 3 the insulin adsorption to the hydrophilic coating is significantly decreased as compared to the coating exhibiting a water contact angle of 105°. The decrease is more than 30%.

What is claimed is:

1. A medical article for containing a pharmaceutical protein preparation comprising at least a first component and a second component, which is in frictional engagement with said first component, wherein such frictional engagement produces long term static frictional forces between said first and second components, wherein at least one surface on either the first or the second component or both is coated independently with a hydrophilic coating, wherein said coating has a surface with a hydrophilicity as measured by a water contact angle, and wherein:

the hydrophilicity of the surface of the coating as measured by the water contact angle is below 600°, and the long term static frictional forces between the first and the second component are below 14 N.

2. The medical article according to claim 1, wherein the coating is a hydrophilized oil or a hydrophilized copolymer.

3. The medical article according to claim 2, wherein the coating comprises a hydrophilized poly(dialkyl siloxane) oil or copolymer.

4. The medical article according to claim 3, wherein the coating comprises a cross-linked or gelled hydrophilizes poly(dialkyl siloxane) oil.

5. The medical article according to claim 3, wherein the coating comprises a hydrophilized poly(dialkyl siloxane) oil having a viscosity above 200,000 centistokes.

6. The medical article according to claim 3, wherein the coating comprises a hydrophilized poly(dialkyl siloxane) block and graft copolymer.

7. The medical article according to claim 3, wherein the poly(dialkyl siloxane) is selected from poly(dimethyl siloxane), poly(dipropyl siloxane) or poly(dihexyl siloxane).

8. The medical article according to claim 1, wherein the coating on the first component comprises a hydrophilized poly(dialkyl siloxane) oil and the coating on the second component comprises a hydrophilized cross-linked poly(dialkyl siloxane) oil.

9. The medical article according to claim 1, wherein the coating is hydrophilized by oxidative treatment.

10. The medical article according to claim 9, wherein the coating hydrophilized by oxidative treatment is further modified by coupling hydrophilic polymer segments or functional groups to the coating.

11. The medical article according to claim 1, wherein the coating comprises a copolymer which is hydrophilized by end-capping the copolymer with hydrophilic group or chain segments.

12. The medical article according to claim 1, wherein the coating has a thickness in the range of 0.005 to 10 $\mu$m.

13. The medical article according to claim 1, wherein the first component is a container made of a material selected from glass, ceramic, metal, plastic and plastic filled with inorganic or organic filler.

14. The medical article according to claim 13, wherein the first component is made of plastic or plastic filled with inorganic or organic filler.

15. The medical article according to claim 1, wherein the second component is a stopper at least partly made of a flexible material.

16. The medical article according to claim 1, wherein the article further comprises mixing means.

17. The medical article according to claim 16, wherein the surfaces of the mixing means are at least partly coated with a coating as defined in claim 1.

18. The medical article according to claim 1, wherein the maximum static friction forces between the first and the second component after 14 days are below 12 N.

19. The medical article according to claim 1, wherein the maximum dynamic friction forces between the first and the second component after 14 days are below 10 N.

20. The medical article according to claim 1, wherein the coating has a thickness in the range of 0.01 to 1 $\mu$m.

21. A process of producing a component of a medical article having at least one surface coated with a coating as defined in claim 1, comprising adding the coating material to the component material prior to molding and subsequently molding the component from the mixture, or molding the component from the component material and subsequently applying the coating material to the at least one surface of the component, and hydrophilizing the coating material prior to the molding or after the molding.

22. The process according to claim 21, wherein the coating is applied by dip coating, spray coating or plasma polymerization.

23. The process according to claim 21, wherein the coating is solubilized prior to application and the solvent removed after application.

24. The process according to claim 21, wherein the coating is cured.

25. The process according to claim 21, wherein the oil or copolymer is hydrophilized by oxidative treatment.

26. The process according to claim 21, wherein the copolymer is hydrophilized by end-capping the copolymers with hydrophilic group or chain segments.

27. The process according to claim 21, wherein the coating has a thickness in the range of 0.005 to 10 $\mu$m.

28. The process according to claim 21, wherein the component is a container made of a material selected from glass, ceramic, metal and plastic.

29. The process according to claim 21, wherein the component is a stopper at least partly made of a flexible material.

30. A coating system for articles having at least a first component and a second component, said second component being in frictional engagement with said first component, wherein such frictional engagement produces long term static frictional forces between said first and second components, wherein said coating system comprises a coating which is applied to at least one surface on either the first or the second component or both, wherein said coating is a hydrophilic coating having a surface with a hydrophilicity as measured by a water contact angle, and wherein:

the hydrophilicity of the surface of the coating as measured by the water contact angle is below 60°, and the long term static frictional forces between the first and the second component are below 14 N.

31. The coating system according to claim 30, wherein the coating is a hydrophilized oil or a hydrophilized copolymer.

32. The coating system according to claim 31, wherein the coating comprises a hydrophilized poly(dialkyl siloxane) oil or copolymer.

33. The coating system according to claim 32, wherein the coating comprises a cross-linked or gelled hydrophilized poly(dialkyl siloxane) oil.

34. The coating system according to claim 32, wherein the coating comprises a hydrophilized poly(dialkyl siloxane) oil having a viscosity above 200,000 centistokes.

35. The coating system according to claim 32, wherein the coating comprises a hydrophilized poly(dialkyl siloxane) block and graft copolymer.

36. The coating system according to claim 32, wherein the poly(dialkyl siloxane) is selected from the group of poly(dimethyl siloxane), poly(dipropyl siloxane), and poly(dihexyl siloxane).

37. The coating system according to claim 30, wherein the coating on the first component comprises a hydrophilized poly(dialkyl siloxane) oil and the coating on the second component comprises a hydrophilized cross-linked poly(dialkyl siloxane) oil.

38. The coating system according to claim 30, wherein the coating is hydrophilized by oxidative treatment.

39. The coating system according to claim 38, wherein the coating hydrophilized by oxidative treatment is further modified by coupling hydrophilic polymer segments or functional groups to the coating.

40. The coating system according to claim 30, wherein the coating comprises a copolymer which is hydrophilized by end-capping the copolymer with hydrophilic group or chain segments.

41. The coating system according to claim 30, wherein the coating has a thickness in the range of 0.005 to 10 $\mu$m.

42. The coating system according to claim 30, wherein the coating has a thickness in the range of 0.01 to 1 $\mu$m.

43. The coating system according to claim 30, wherein the maximum static friction forces between the first and the second component after 14 days are below 12 N.

44. The coating system according to claim 30, wherein the maximum dynamic friction forces between the first and the second component after 14 days are below 10 N.

* * * * *